US006435872B1

(12) United States Patent
Nagel

(10) Patent No.: US 6,435,872 B1
(45) Date of Patent: *Aug. 20, 2002

(54) TAPERED LIGHT PROBE WITH NON-CIRCULAR OUTPUT FOR A DENTAL LIGHT CURING UNIT

(75) Inventor: Rich Nagel, Chicago, IL (US)

(73) Assignee: Bisco, Inc., Schaumburg, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/496,447

(22) Filed: Feb. 2, 2000

(51) Int. Cl.$^7$ ................................................. A61C 1/00
(52) U.S. Cl. ....................................................... 433/29
(58) Field of Search ................... 433/29, 141; 604/902, 604/119; 385/902, 115; 362/572, 573, 556

(56) References Cited

U.S. PATENT DOCUMENTS

| | | | | |
|---|---|---|---|---|
| 4,597,030 A | * | 6/1986 | Brody et al. | 385/115 |
| 5,208,890 A | * | 5/1993 | Kohler et al. | 385/115 |
| 5,290,169 A | * | 3/1994 | Friedman et al. | 433/29 |
| 5,335,306 A | * | 8/1994 | Takita et al. | 385/115 |
| 5,371,826 A | * | 12/1994 | Friedman et al. | 385/115 |
| 5,415,543 A | * | 5/1995 | Rozmajzi, Jr. | 433/29 |
| 5,759,032 A | * | 6/1998 | Bartel | 433/29 |
| 5,797,740 A | * | 8/1998 | Lundvik | 433/29 |
| 5,882,197 A | * | 3/1999 | Davis et al. | 433/29 |
| 6,179,830 B1 | * | 1/2001 | Kokubu | 433/29 |
| 6,200,134 B1 | * | 3/2001 | Kovac et al. | 433/29 |

FOREIGN PATENT DOCUMENTS

| | | | | |
|---|---|---|---|---|
| EP | 240007 | * | 10/1987 | 433/29 |
| EP | 0750889 A1 | | 1/1997 | |
| WO | 93/13729 | * | 7/1993 | 433/29 |
| WO | WO 99/21505 | | 6/1999 | |

OTHER PUBLICATIONS

3M Curing Lights/3M Dental Products catalog.
Acta c.w.s./Amadent Corp. catalog.
Clearfil AP–X/J. Morita catalog.
Coltolux/colténe whaledent catalog.
Dental Health Products, Inc. fall/winter catalog.
Elipar Highlight/ESPE America Catalog.
Fen Dental Mfg. Inc. catalog.
Halogen–Curling Lamp/carlo de giorgi catalog.
Heliolux DLX/Vivadent catalog.
Heliolux DLX/Ivoclar Vivadent catalog.
Hilux /Benlioglu Dental Inc. catalog.
Kerr Demetron/Sybron Dental Specialties.
NL 15/Halogen–Light unit catalog.
Nou Lite 10/Halogen–Light unit catalog.
ProMix/Dentsply Caulk catalog.
QHL75/Dentsply Caulk catalog.
Spectrum/Dentsply Caulk catalog.
Sunlite 1275/Fen Dental Manufacturing, Inc. catalog.
Spring Health Products, Inc.97–1 catalog.

* cited by examiner

Primary Examiner—Todd E. Manahan
(74) Attorney, Agent, or Firm—Howrey Simon Arnold & White, LLP

(57) ABSTRACT

A light probe and a method of using a light probe for curing dental resin in relatively small areas such as at the adhesive interface between a tooth and an orthodontic bracket are disclosed. The light probe is attachable to the curing gun and includes an optically transparent medium extending from a connection end to a discharge end. The medium is disposed at the discharge end such that only a thin ribbon of light is emitted. The cross-sectional area of the discharge end is substantially smaller than at the connection end, and the overall area of discharge is smaller than the input area. An edge of the discharge end of the light probe is placed against the surface of the tooth and light is emitted parallel to the surface of the tooth onto a plane of adhesive.

32 Claims, 3 Drawing Sheets

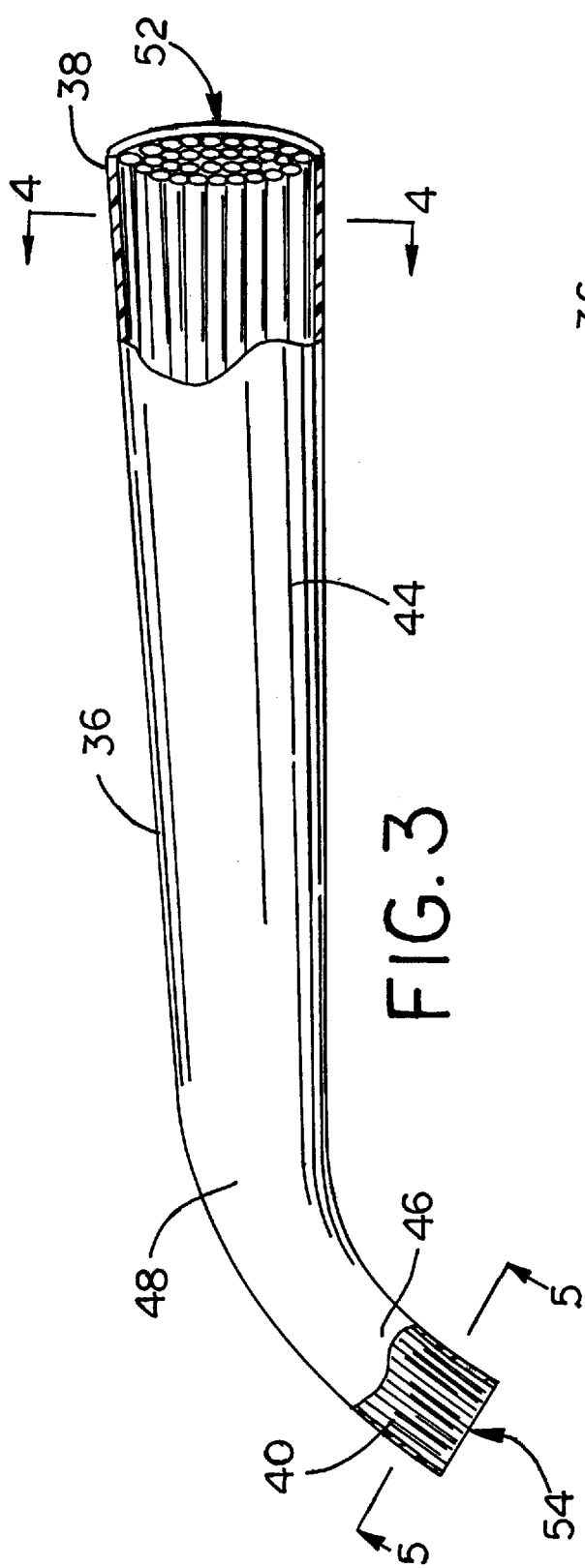
FIG.3
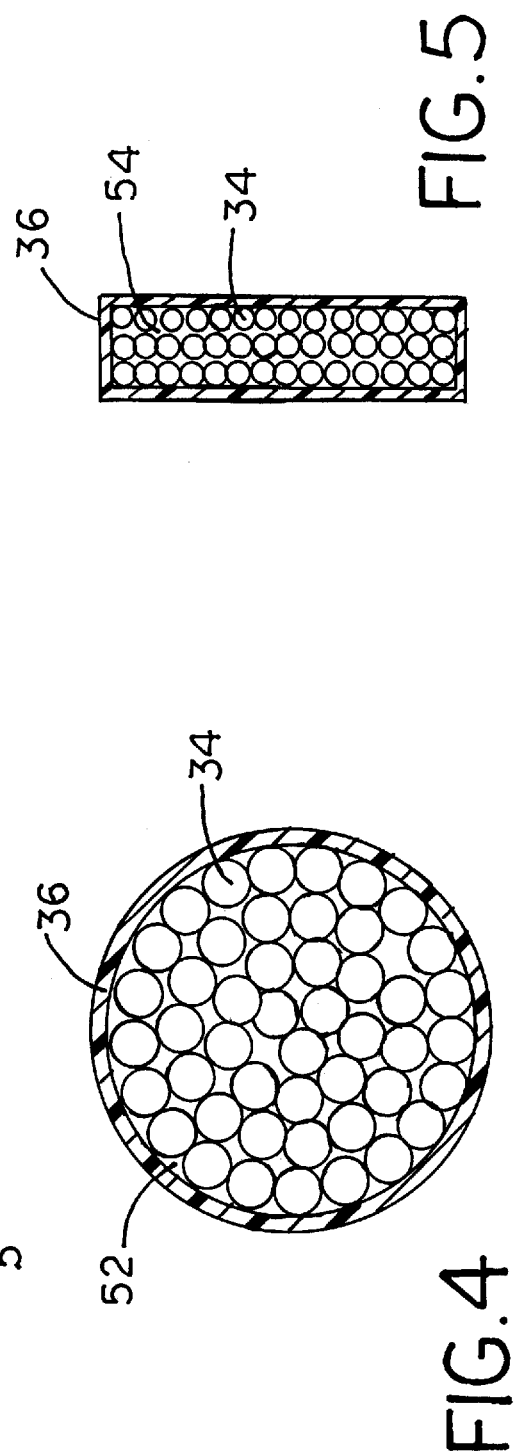
FIG.4
FIG.5

TAPERED LIGHT PROBE WITH NON-CIRCULAR OUTPUT FOR A DENTAL LIGHT CURING UNIT

BACKGROUND OF THE INVENTION

1. Field of the Invention

The invention relates generally to dental tools and, more particularly, the invention relates to tools using light to cure dental materials containing resins.

2. Description of Related Technology

Dental restoration procedures often require various resin containing materials such as composites and adhesives to be filled into a tooth cavity or area being repaired, and subsequently cured. With certain restoration procedures, the filling and curing cycle may be repeated several times. The curing process is often performed using a curing tool, which emits light from a source, such as a bulb, and through a bundle of optic fibers, to thus result in a focused light output. The light output is directed at the resin and the resin is quickly cured by polymerization.

To facilitate the curing process, the fiber optic bundle may be provided within a probe or light guide extending from the curing tool or gun. The probe may extend linearly from the gun with an angular cant toward a distal end to enable the operator to more easily access the tooth being repaired.

Prior art light probes are typically 8–13 mm in diameter, and utilize a round tip at the distal end. Light from the dental curing gun is communicated through the light probe along the optic fiber bundle and exits the distal end in a circular pattern which is applied to a dental resin for curing. In order to quicken the curing process, some light probes have used a smaller cross-sectional area at the distal end being drawn from a larger cross-sectional area at a proximal end. In this manner, the light from the curing gun is amplified by being drawn into a smaller cross-sectional area and focused on the area being cured, resulting in faster curing cycles.

However, some areas which require curing are significantly smaller than others or are uniquely shaped. For example, when curing a plane of adhesive between the surface of a tooth and an orthodontic bracket, the area of exposure can be considerably smaller than that of typical tooth restoration, such as cavity fillings. In such cases, light being delivered from a round tip is not always efficiently projected across the interface, resulting in application over areas that do not need to be cured. This does not optimize the useful intensity of the light, thus resulting in an inefficient light probe.

SUMMARY OF THE INVENTION

According to the invention, a light probe for use with a dental curing gun includes a first end and a second end, the second end having a non-circular cross-section. The light probe further includes a straight section between the first and second ends, with an optically transparent medium extending through the straight section from the first end to the second end.

Other aspects and features of the invention may become more apparent from the following detailed description when taken in conjunction with the accompanying drawings and the appended claims.

BRIEF DESCRIPTION OF THE DRAWINGS

FIG. 3 is an elevational side view of the light probe of FIGS. 1 and 2 with a partial cutaway revealing the fiber optic bundle.

FIG. 4 is a cross-sectional view of the fiber bundle of FIG. 3 taken at line 4—4.

FIG. 5 is a cross-sectional view of the fiber bundle of FIG. 3 taken at line 5—5.

DETAILED DESCRIPTION OF A PREFERRED EMBODIMENT

Figure 1:
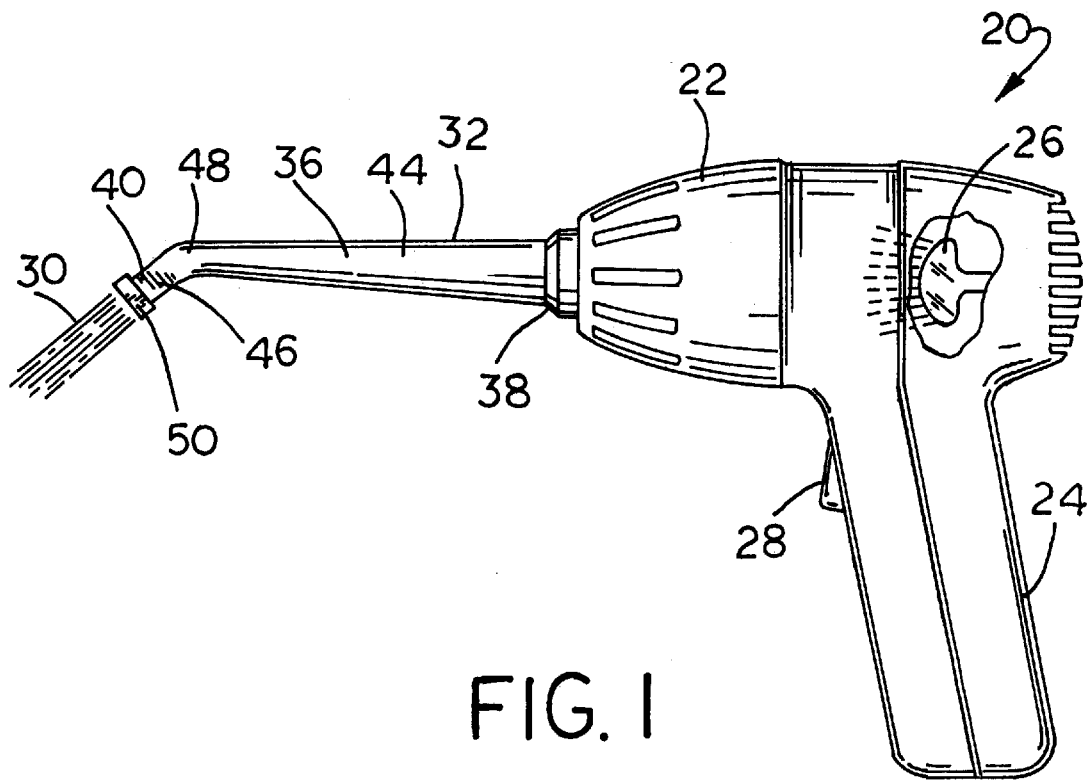
FIG. 1 is an elevational side view of a dental curing gun employing a light probe constructed in accordance with the invention.

Referring now to the drawings, and with specific reference to FIG. 1, a dental curing gun according to the invention is generally depicted by reference numeral 20. As shown therein, the curing gun 20 may include a barrel 22 and a grip 24. The barrel 22 may house a light source, such as a bulb 26 (a tungsten halogen lamp, for example) adapted to emit light when an electrical circuit thereto is closed by a trigger 28. The curing gun 20 is connected to a power source (not shown), which is typically AC power, although battery power is possible. The elements of the gun 20 may vary from tool to tool, and simply serve as background environment for the invention.

When the trigger 28 is actuated, light (designated 30) is emitted by the bulb 26 and directed through the probe 32. The probe 32 typically includes a plurality of fiber optic fibers 34 wrapped in a protective sheath or conduit 36 as shown in FIGS. 4 and 5. Alternatively, a solid, optically transparent material, such as glass or plastic, may be utilized in lieu of individual fibers. The conduit 36 maybe manufactured from any suitable material, including fused glass. As shown, the conduit 36 may include a connection end 38 and a discharge end 40. The connection end 38 is typically provided with an attachment mechanism 42 to allow the probe 32 to be readily attached and detached from the gun 20, for purposes such as replacement or sterilization. A straight section 44 extends from the connection end 38 and merges into a canted section 46 proximate the discharge end 40. A nexus 48 (illustratively bent) defines the merger between the straight section 44 and the canted section 46. A protective rim 50 may be provided at the discharge end 40 to protect the end faces of the optic fibers 34. The rim 50 may be adhered to the probe 32 with a suitable adhesive, such as an epoxy adhesive.

Figure 2:
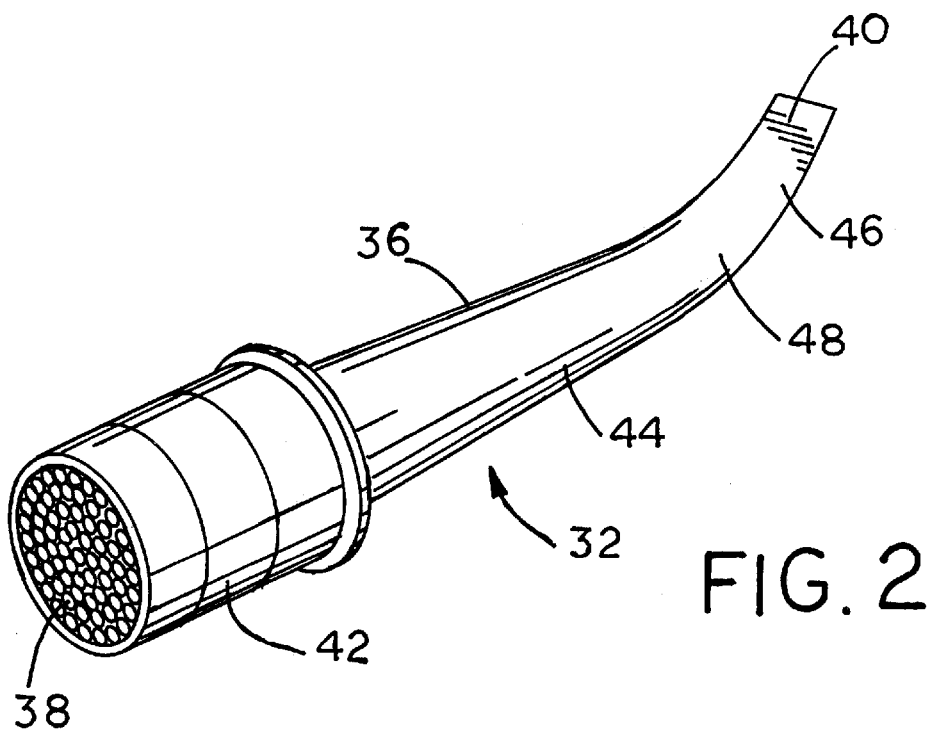
FIG. 2 is a perspective view of the light probe of FIG. 1 unattached from the curing gun.

As seen best in FIG. 2, the conduit 36 tapers along its length from a relatively large, preferably circular, input area at its connection end 38 to a relatively thin non-circular ribbon at the discharge end 40. The overall size and area of the output may vary, but may be provided at, for example, a ratio of 3:1 (input area to output area), with a overall probe length of 15 mm. Such a probe increases light intensity, defined as light flux per unit area, by a factor of three. Preferably, the size of the output is comparable in size to the dental area being worked. For example, a thin ribbon-type output may be the most efficient way of applying light to adhesive at a tooth/bracket interface, but other output shapes including, but not limited to, triangles, tetragons, polygons, and the like are possible.

Since a fixed number of optic fibers 34 are positioned within the conduit 36, each optic fiber 34 is specifically oriented within the conduit and aggregately reduced in diameter along a longitudinal axis of the conduit 36 in order to output light in an intensified, non-circular or substantially linear pattern. As can be seen in FIGS. 3–5, the fibers 34 are arranged at the connection end 38 in a cylindrical bundle 52 having a substantially round cross-sectional input area. As the fibers 34 traverse the length of the conduit 36, the fiber optics form an aggregate bundle 54 having a non-circular or substantially linear cross-sectional output. Thus, at the discharge end 40, the cross-section will be non-circular or substantially linear. The optic fibers 34 are reduced in diameter by tapering along their length, in correspondence with the tapering of the conduit 36. The fibers 34 may be tapered by heating and stretching techniques, so that each fiber 34 has a larger diameter at the connection end 38 than at the discharge end 40. The fiber bundle thus has a larger cross-sectional area at the connection end 38 (see FIG. 4), and a significantly smaller cross-sectional area at the discharge end 40 (see FIG. 5).

Referring to FIGS. 1 and 2, light 30 from the curing gun 20 is coupled into the fiber optic bundle input at the connection end 38. As the light 30 is communicated along the conduit 36, the light intensity is significantly amplified as the cross-sectional area of the fiber bundle gets smaller, because the light 30 is being drawn into a smaller area. Upon output at the discharge end 40, the light 30 is arranged in a non-circular or substantially linear pattern.

Figure 6:
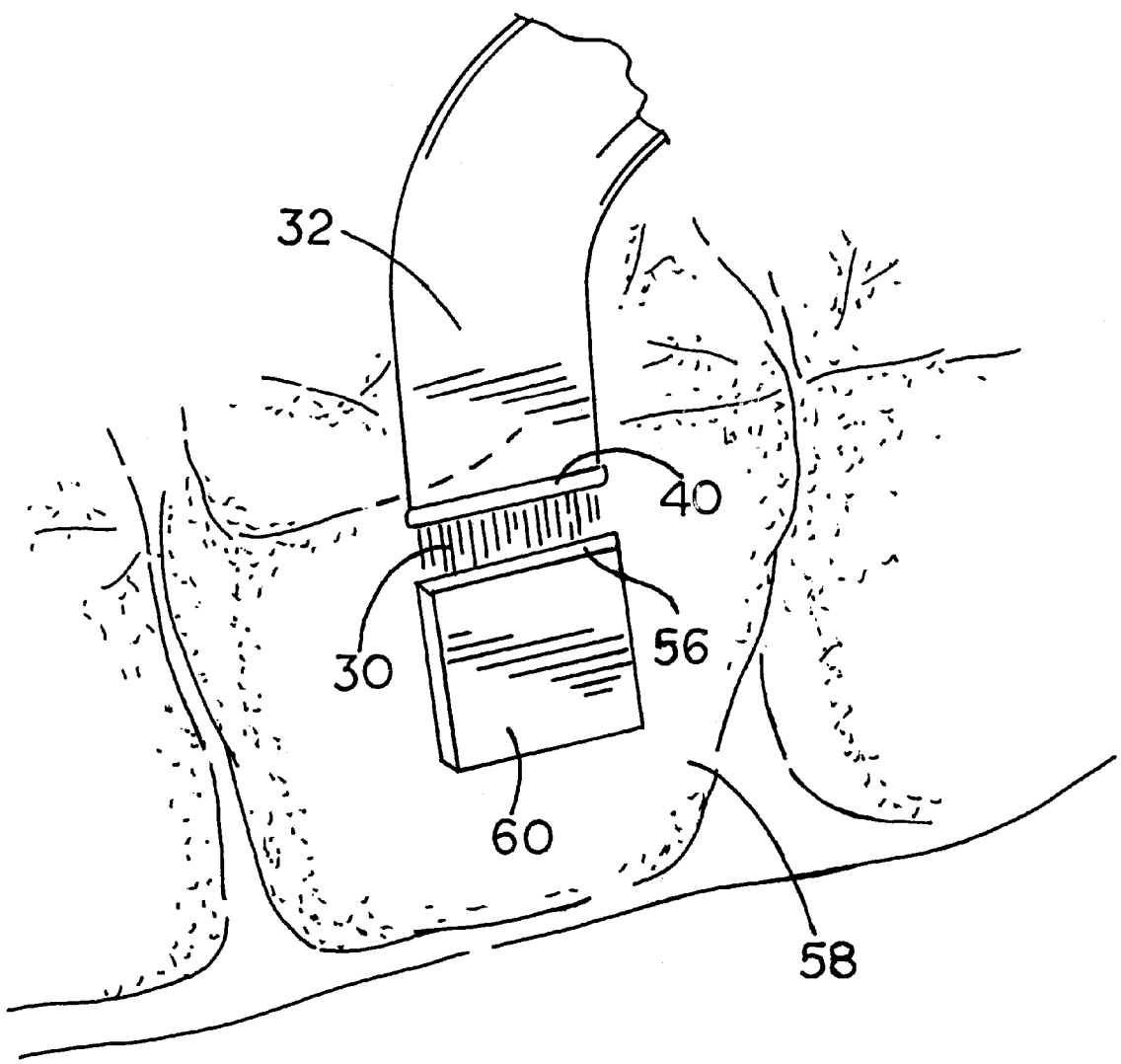
FIG. 6 is a view of the light probe of the invention being used in conjunction with a curing gun to secure an orthodontic bracket to a tooth.

As shown in FIG. 6, when the light pattern is applied to the area of exposure of an adhesive 56, the light 30 is efficiently arranged along a line projected across a plane of the adhesive 56 between a surface of a tooth 58 and an orthodontic bracket 60. The light 30 is only applied where it is needed, thereby optimizing the useful intensity of the light 30.

Preferably, the edge of the discharge end 40 is placed along the edge of the tooth 58. The light 30 exits parallel to the surface of the tooth 58 so as to project the light 30 across the plane of the adhesive 56.

The intensity of the light 30 in the smaller, non-circular or linear area of the discharge end 40 is comparable to that of a plasma arc lamp or laser, resulting in quick and efficient curing cycles. The light probe 32, as described above, combined with a curing gun 20 provides light intensity and curing speeds for orthodontic bracket attachment that are comparable to plasma arc lamps or lasers, but at substantially less cost.

While the present invention has been described with reference to specific examples, which are intended to be illustrative only, and not to be limiting of the invention, it will be apparent to those of ordinary skill in the art that changes, additions or deletions may be made to the disclosed embodiments without departing from the spirit and scope of the invention.

What is claimed is:

1. A light probe for a dental curing gun, the light probe comprising:
    an input end having a cross-sectional area;
    an output end having a non-equilateral cross-sectional area, the output end cross-sectional area being smaller than the input end cross-sectional area;
    the output cross-sectional area having a longitudinal axis that is greater in length than its lateral axis,
    a substantially straight section positioned between the input and output ends for transmitting light from the input end to the output end; and
    an optically transparent media extending through the straight section from the input end to the output end.

2. The light probe of claim 1 further comprising a canted section positioned between the substantially straight section and the output end.

3. The light probe of claim 1 further comprising an attachment mechanism on the input end to attach the probe to a light curing gun.

4. The light probe of claim 1 further comprising a protective rim proximate the output end.

5. The light probe of claim 1 wherein the cross-sectional area of the output end smaller than the cross-sectional area of the input end.

6. The light probe of claim 1 wherein the optically transparent medium comprises a plurality of optical fibers.

7. The light probe of claim 1 wherein the optically transparent medium consists of a unitary solid, optically transparent material.

8. The light probe of claim 1 wherein the output end of the light probe has a substantially elliptical, oval or oblong cross-sectional area.

9. The light probe of claim 1 wherein the output end of the light probe has a substantially rectangular cross-sectional area.

10. The light probe of claim 1 having an input end cross-sectional area to output end cross-sectional area ratio of at least about 3:1.

11. The light probe of claim 10 wherein the light probe has a length of at least about 15 mm.

12. The light probe of claim 1 wherein light transmitted through the probe is increased in intensity by a factor of at least about three.

13. A light probe comprising:
    a fiber optic conduit having a first end, a second end, and a core connecting the first and second ends, the first end having a cross-sectional area, the second end having a non-equilateral cross-sectional area, the first end cross-sectional area being greater than the second end cross-sectional area;
    the output cross-sectional area having a longitudinal axis that is greater in length than its lateral axis, and
    one or more optical fibers extending through a core of the conduit from the first end to the second end.

14. The light probe of claim 13 wherein the first end has a cross-sectional area larger than the cross-sectional area of the second end.

15. The light probe of claim 14, wherein the first end is an optical input, the second end is an optical output, and the one or more fiber optics are adapted to amplify light intensity.

16. The light probe of claim 13, wherein the second end has a substantially elliptical, oval or oblong cross-sectional area.

17. The light probe of claim 13, wherein the first end has a circular cross-sectional area.

18. The light probe of claim 13, wherein the second end has a substantially rectangular cross-sectional area.

19. A light probe for communicating light from a light source to a point of application, the light probe comprising an optical fiber bundle having a first end, a second end, and a plurality of fibers disposed in a substantially non-equilateral tetragonal pattern at the second end, the second end having a cross-sectional area having a longitudinal axis that is greater in length than its lateral axis.

20. The light probe of claim 19 wherein the plurality of fibers form an aggregate, the aggregate having a first cross-sectional area at the second end.

21. The light probe of claim 19 wherein the fiber bundle is enclosed within a protective sheath.

22. A method of using a light probe for curing dental material containing resins, the light probe having a plurality of optically transparent media disposed in a substantially linear pattern at an output end, the method comprising the steps of:

positioning the output end of the light probe adjacent the dental material; and applying light from the output onto the material in a substantially linear pattern.

23. The method of claim 22 wherein light transmitted through the probe during the applying step increases in intensity by a factor of at least about three.

24. A dental curing gun light probe adapted to emit light toward a target dental installation, the probe comprising:

an input end adapted to be connected to a dental curing gun; and an output end having a non-equilateral cross-sectional shape substantially corresponding to the cross-sectional shape of the target dental installation, the output cross-sectional shape having a longitudinal axis that is greater in length than its lateral axis.

25. The dental curing gun light probe of claim 24, wherein the target dental installation and output end have substantially rectangular cross-sectional shapes.

26. The dental curing gun light probe of claim 24, wherein the target dental installation and output end have substantially elliptical, oval or oblong cross-sectional shapes.

27. The dental curing gun light probe of claim 24, wherein the probe tapers from the input end to the output end.

28. The dental curing gun light probe of claim 24, wherein the input end has a substantially circular cross-sectional area, and the output end has a substantially rectangular cross-sectional area.

29. A method of curing a target dental installation, comprising the steps of:

ascertaining the geometric shape of a target dental installation;

emitting light toward the dental installation, the light being emitted in a beam having a non-equilateral cross-sectional shape substantially matching the cross-sectional shape of the dental installation, the beam having a cross-sectional area having a longitudinal axis that is greater in length than its lateral axis.

30. The method of claim 29, further including the step of adhering an orthodontic bracket to a tooth using adhesive, and wherein the target dental installation is the adhesive.

31. The method of claim 30, wherein the geometric shape of the target dental installation is substantially linear.

32. The method of claim 29, wherein the emitting light step is performed using a light emitting probe extending from a dental curing gun.

* * * * *